United States Patent
Dlubala et al.

(10) Patent No.: US 8,258,298 B2
(45) Date of Patent: Sep. 4, 2012

(54) SYNTHESIS OF MORPHINE-6-GLUCURONIDE OR ONE OF THE DERIVATIVES THEREOF

(75) Inventors: Alain Dlubala, Paris (FR); Claire Trecant, Strasbourg (FR); Isabelle Ripoche, Aubiere Cedex (FR)

(73) Assignee: Sanofi, Paris (FR)

( * ) Notice: Subject to any disclaimer, the term of this patent is extended or adjusted under 35 U.S.C. 154(b) by 0 days.

(21) Appl. No.: 13/155,646

(22) Filed: Jun. 8, 2011

(65) Prior Publication Data

US 2011/0275820 A1 Nov. 10, 2011

Related U.S. Application Data

(63) Continuation of application No. PCT/FR2009/052445, filed on Dec. 8, 2009.

(30) Foreign Application Priority Data

Dec. 10, 2008 (FR) .................................. 08 06948

(51) Int. Cl.
*C07D 489/02* (2006.01)
(52) U.S. Cl. ......................................................... 546/44
(58) Field of Classification Search .................. 546/44
See application file for complete search history.

(56) References Cited

U.S. PATENT DOCUMENTS

| | | | |
|---|---|---|---|
| 3,766,188 A | 10/1973 | Murakami et al. | |
| 2003/0022876 A1* | 1/2003 | Ashton et al. ................ | 514/176 |
| 2007/0116665 A1 | 5/2007 | Temsamani et al. | |

FOREIGN PATENT DOCUMENTS

| | | |
|---|---|---|
| FR | 2864082 | 6/2005 |
| WO | WO 93/03051 | 2/1993 |
| WO | WO 95/05831 | 3/1995 |
| WO | WO 98/46618 | 10/1998 |
| WO | WO 99/64430 | 12/1999 |
| WO | WO 2005/063263 | 7/2005 |

OTHER PUBLICATIONS

U.S. Appl. No. 13/155,655, filed Jun. 8, 2011, Dlubala, et al.
U.S. Appl. No. 13/155,727, filed Jun. 8, 2011, Dlubala, et al.
Yoshimura, H., et al., Metabolism of Drugs. LX. 1) The Synthesis of Codeine and Morphine Glucuronides 2), Chem. Pharm. Bull., vol. 16, No. 11, pp. 2114-2119, (1968).
Abdel-Monem, M. M., et al., N-Demethylation of Morphine and Structurally Related Compounds With Chloroformate Esters, Journal of Medicinal Chemistry, vol. 15, No. 2, (1972), pp. 208-210.
Auterhoff, et al., Die Farbreaktion dea Morphins Nach E. Marquis, Archiv Dsr Pharmazie (Weinheim), vol. 306, No. 11, (1973), pp. 866-872.
Berrang, B., et al., Synthesis of Morphine-3,6-di-B-D-Giucuronide, Synthesis, (1997), pp. 1165-1168.
Brown, R. T., et al., A Simple Synthesis of Morphine-3,6-di-B-D-Giucuronide, Tetrahedron, vol. 56, (2000), pp. 7591-7594.
Cheng, G., et al., Syn Additions to 4a-Epozypyranosides: Synthesis of L-Idopyranosides, Organic Letters, vol. 9, No. 23, pp. 4849-4852, (2007).
D'Amour, et al., A Method for Determining Loss of Pain Sensation, Journal of Pharmacology and Exp. Ther., vol. 72, pp. 74-79, (1941).

Danishefsky, S. J., et al., A Stereoselective Totally Synthesis Route to Methyl a-Peracetylhikosaminide, J. Am. Chem. Soc., (1989), vol. 111, pp. 2193-2204.
Frances, B., et al., Further Evidence That Morphine-6B-Glucuronide is a More Potent Opioid Agonist Than Morphine, The Journal of Pharmacology and Experimental Therapeutics, vol. 262, No. 1, pp. 25-31, (1992).
Frensch, K., et al., Notiz Uber Oligoethylenglykolether des Morphins, Liebigs Ann. Chem. (1979), pp. 2118-2120.
McMillan, K. G., et al., Synthesis, Structure and Reactivity of 5-Pyranosyl-1,3,4-Oxathiazol-2-Ones, Carbohydrate Research, vol. 341, (2006), pp. 41-48.
Nakajima, R., et al., Synthesis of Methyl 1-O-(4-Hydroxymethamphetaminyl)-a-D-Glucopyranouronate, Chem. Pharm. Bull., vol. 53, No. 6, pp. 684-687, (2005).
Narta, M., et al., Regulations of Opioid Dependence by Opioid Receptor Types, Pharmacology & Therapeutics, vol. 89, (2001), pp. 1-15.
Paul, D., et al., Pharmacological Characterization of Morphine-6B-Glucuronide, A Very Potent Morphine Metabolite, The Journal of Pharmacology and Experimental Therapeutics, (1989), vol. 251, pp. 477-483.
Vlahov, J., et al., Uber Eine Verbesserte Synthese Von B-Glucosiduronsaure-Derivaten, Liebigs Ann. Chem., (1983), pp. 570-574.
International Search Report for International Application No. PCT/FR2009/052445—Publication No. WO2010/067007.

* cited by examiner

*Primary Examiner* — Charanjit Aulakh
(74) *Attorney, Agent, or Firm* — Robert Kajubi; Kelly Bender

(57) ABSTRACT

The disclosure relates to a method for preparing morphine-6-glucuronide or one of the deritives thereof comprising reacting a compound of formula (I):

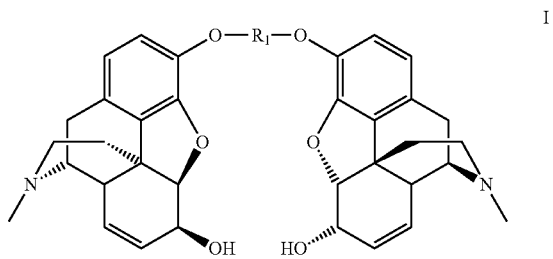

wherein $R_1$ is as defined in the disclosure,
with a glucuronic acid derivative of formula (II):

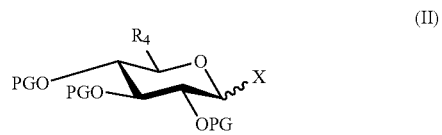

wherein PG, X, and $R_4$ are as defined in the disclosure,
in the presence of an aromatic solvent and trimethylsilyl trifluoromethanesulfonate;
(ii) reacting the product obtained in step (i) with a strong basic agent; and then (iii) recovering the product obtained in step (ii).

14 Claims, No Drawings

SYNTHESIS OF MORPHINE-6-GLUCURONIDE OR ONE OF THE DERIVATIVES THEREOF

This application is a continuation of International application No. PCT/FR2009/052445, filed Dec. 8, 2009, which is incorporated herein by reference in its entirety; which claims the benefit of priority of French Patent Application No. 0806948, filed Dec. 10, 2008.

FIELD OF THE INVENTION

The present invention relates to a process for preparing morphine-6-glucuronide (M6G) or a derivative thereof.

DESCRIPTION OF THE CONTEXT OF THE INVENTION

Morphine is currently the analgesic the most widely used in the treatment of pain of moderate to strong intensity. This opioid is used in about 80% of cases of post-operative acute pain. Despite its high efficacy, the use of morphine is accompanied by many undesirable side effects, characteristic of opioids, such as respiratory depression, nausea, vomiting, inhibition of intestinal transit, dependence and tolerance (Minoru Nariata et al., *Pharmacol. Et Ther.* 2001, 89, 1-15).

It is known that morphine undergoes substantial metabolism leading especially to the formation of morphine-6-glucuronide (M6G). This metabolite penetrates poorly into the brain on account of its hydrophilic nature. It has stronger analgesic activity than that presented by morphine via central administration, with a decrease in respiratory depression, nausea and vomiting (Paul et al., *J. Pharmacol. Exp. The* 1989, 251, 477-483; Frances et al., *J. Pharmacol. Exp. The* 1992, 262, 25-31). Patent application WO 95/05831 describes the use of M6G in oral form for treating pain.

M6G was synthesized in 1968 by Yoshimurai et al. (Yoshimura, H.; Oguri, K.; Tsukamoto, H. *Chem. Pharm. Bull.* 1968, 16, 2114-2119). At the industrial scale, this process, which is based on the Koenigs-Knorr principle, is of poor yield. Furthermore, the heavy metals present in trace amount in the final product are difficult to remove. Finally, the silver salts must be recycled. A process for synthesizing M6G via the synthesis of a glycosyl donor in ortho ester form in the presence of lutidinium perchlorate was moreover proposed in patent application WO 99/64430. However, this method only gives a poor glycosylation yield, of about 30%. Moreover, these methods, which involve a glycosylation in heterogeneous medium with stirring, are difficult to implement at the industrial scale.

Other methods for performing the O-glycosylation have been envisioned, especially via activation in the form of an imidate or a thioaryl. These procedures, which require implementation under particular conditions, namely strictly anhydrous conditions, i.e. a water content of less than 100 ppm, and low temperature, impose major constraints at the industrial level. Furthermore, activation via a thioaryl intermediate generally uses thiophenol, which gives off a nauseating odor that is a problem in the context of implementation at the industrial scale.

There is thus still a need for a process for producing such derivatives at the industrial scale, not only in a high yield but also with a minimum of technical constraints.

The aim of the present invention is to propose a process for preparing M6G or a derivative thereof in a yield of at least 60%, the glycosylation step of which is performed in homogeneous medium, which is tolerant to moisture, i.e. which supports a water content ranging up to 3000 ppm, and which can be performed at a temperature of about 20° C.

This aim is achieved via the process according to the invention, which comprises the combined use of a glycosyl derivative with trihaloacetimidate as donor of glycosylated derivatives and dimorphine derivatives as acceptor of glycosylated derivatives, making it possible to obtain very good stereoselectivity.

A process with a satisfactory yield that has a minimum of industrial constraints has now been found.

Thus, according to a first aspect, the present invention is directed toward a process for preparing M6G or a derivative thereof, comprising the steps consisting in:
reacting a compound corresponding to formula (I) below:

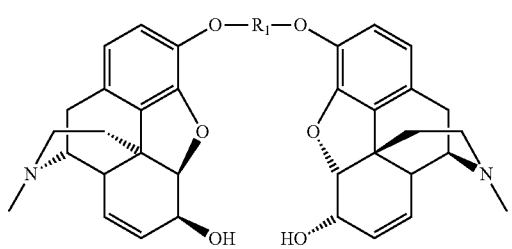

in which:
$R_1$ represents a carbonyl group, $COR_5CO$ in which $R_5$ represents a group $(C_1-C_4)$alkane-diyl, $(C_2-C_4)$alkene-diyl, $(C_2-C_4)$alkyne-diyl, hetero$(C_1-C_4)$alkane-diyl, heterocyclo$(C_3-C_6)$alkane-diyl, $(C_5-C_{14})$arene-diyl, hetero$(C_4-C_{10})$arene-diyl, bi$(C_{10}-C_{16})$arene-oxide-diyl, or bi$(C_{10}-C_{16})$arene-diyl, $SO_2R_6SO_2$ in which $R_6$ represents a group $(C_1-C_4)$alkane-diyl, $(C_2-C_4)$alkene-diyl, $(C_2-C_4)$alkyne-diyl, hetero$(C_1-C_4)$alkane-diyl, heterocyclo$(C_3-C_6)$alkane-diyl, $(C_5-C_{14})$arene-diyl, hetero$(C_4-C_{10})$arene-diyl, bi$(C_{10}-C_{16})$arene-oxide-diyl or bi$(C_{10}-C_{16})$arene-diyl, with a glucuronic acid derivative corresponding to formula (II) below:

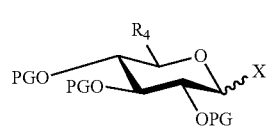

in which:
PG represents an acetyl, isobutyryl, benzoyl or pivaloyl group,
X represents a trihaloacetimidate group, and
$R_4$ represents a group $(C_1-C_4)$alkylcarboxylate,
in the presence:
of an aromatic solvent that is unsubstituted or substituted with one or more substituents chosen from the group formed by a halogen atom, a group $(C_1-C_4)$alkyl and a group $(C_1-C_4)$alkyloxy, said solvent having a melting point of less than or equal to −20° C., and
of trimethylsilyl trifluoromethanesulfonate
(ii) in reacting the product obtained in step (i) with a strong basic agent, and then
(iii) in recovering the product obtained in step (ii).

A subject of the present invention is also the compounds corresponding to formula (III) below

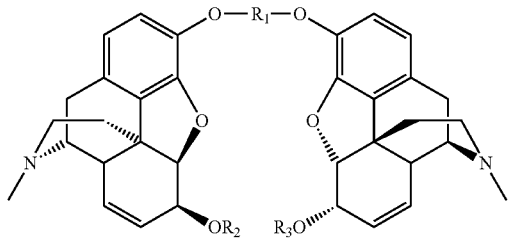

in which:
$R_1$ is as defined previously,
$R_2$ and $R_3$ independently represent a group PG as defined previously or a group corresponding to formula (IV) below:

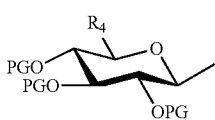

in which:
$R_4$ and PG are as defined previously,
with the proviso that at least one from among $R_2$ and $R_3$ represents a group of formula (IV).

A subject of the present invention is also the compounds corresponding to formula (I) below:

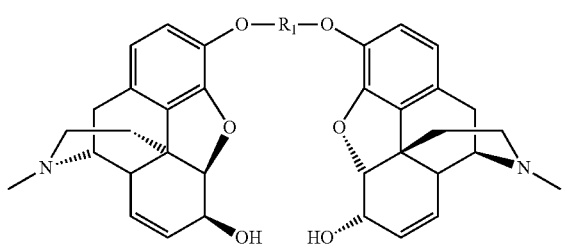

in which:
$R_1$ is as defined previously.

DEFINITIONS

In the context of the present invention, the following definitions apply:
- a group PG: a protecting group that makes it possible, firstly, to protect a reactive function such as a hydroxyl or an amine during a synthesis, and, secondly, to regenerate the intact reactive function at the end of the synthesis; examples of protecting groups and of protection and deprotection methods are given in "Protective Groups in Organic Synthesis", Greene et al., $2^{nd}$ Edition (John Wiley & Sons, Inc., New York), 1991; mention will be made in particular of acetyl, isobutyryl, benzoyl and pivaloyl groups;
- a halogen atom: a fluorine atom, a chlorine atom, a bromine atom or an iodine atom;
- a group $(C_1\text{-}C_4)$alkyl: a substituted or unsubstituted, linear or branched saturated aliphatic group containing from 1 to 4 carbon atoms; examples that may be mentioned include methyl, ethyl, propyl, isopropyl, butyl, isobutyl, tert-butyl, etc. groups;
- a hydroxyl group: a group —OH;
- a group $(C_1\text{-}C_4)$alkyloxy: a group —O—$(C_1\text{-}C_4)$alkyl in which the group $(C_1\text{-}C_4)$alkyl is as defined previously;
- a carbonyl group, a group C=O;
- a group $(C_1\text{-}C_4)$alkane-diyl, a substituted or unsubstituted, linear, branched or cyclic divalent saturated aliphatic group, containing from 1 to 4 carbon atoms; examples that may be mentioned include methane-diyl (—$CH_2$—), ethane-diyl (—$CH_2$—$CH_2$—), propane-2,3-diyl (—$CH(CH_3)CH_2$—), propane-1,3-diyl (—$CH_2$—$CH_2$—$CH_2$—); etc. groups;
- a group $(C_2\text{-}C_4)$alkene-diyl, a linear or branched, monounsaturated or polyunsaturated divalent aliphatic group, containing from 2 to 4 carbon atoms, comprising, for example, one or two ethylenic unsaturations; examples that may be mentioned include ethene-diyl (—CH=CH—), 1-propene-1,3-diyl (—$CH_2$—CH=CH—), etc. groups;
- a group $(C_2\text{-}C_4)$alkyne-diyl, a linear or branched, monounsaturated or polyunsaturated divalent aliphatic group, containing from 2 to 4 carbon atoms, comprising, for example, one or two acetylenic unsaturations; examples that may be mentioned include ethyne-diyl (—C≡C—) and 1-propyne-1,3-diyl (—C≡C—$CH_2$—) groups;
- a group $(C_5\text{-}C_{14})$arene-diyl, a substituted or unsubstituted divalent cyclic aromatic group preferably containing between 5 and 14 carbon atoms; examples that may be mentioned include the groups

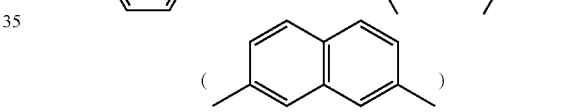

- a group hetero$(C_1\text{-}C_4)$alkane-diyl, a substituted or unsubstituted alkane-diyl group, as defined above, preferably containing between 1 and 4 carbon atoms, comprising one or more heteroatoms, such as nitrogen, oxygen or sulfur; an example that may be mentioned is the ether oxide-diyl group;
- a group heterocyclo$(C_3\text{-}C_6)$alkane-diyl, a substituted or unsubstituted group cyclo$(C_3\text{-}C_6)$alkane-diyl, as defined above, preferably containing between 3 and 6 carbon atoms, comprising one or more heteroatoms, such as nitrogen, oxygen or sulfur; examples that may be mentioned include oxirane-diyl, aziridine-diyl, thirane-diyl and pyran-diyl groups;
- a group hetero$(C_4\text{-}C_{10})$arene-diyl, a divalent cyclic aromatic group preferably containing between 4 and 10 carbon atoms and comprising one or more heteroatoms, such as nitrogen, oxygen and sulfur; examples that may be mentioned include the groups

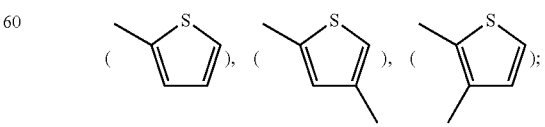

- a group bi$(C_{10}\text{-}C_{16})$arene-diyl, a divalent group comprising two aromatic rings, each possibly being independently substituted or unsubstituted, preferably containing from 10 to 16 carbon atoms; mention may be made of the group

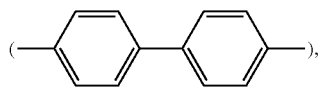

a group bi($C_{10}$-$C_{16}$)arene-oxide-diyl, a divalent group comprising two aromatic rings, each independently substituted or unsubstituted, containing from 10 to 16 carbon atoms; an example that may be mentioned is the group

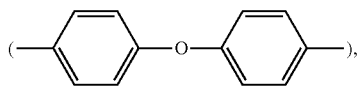

and a group —($C_1$-$C_4$)alkylcarboxylate, a group —CO—O—($C_1$-$C_4$)alkyl, the group ($C_1$-$C_4$)alkyl being as defined above.

The expression "strong basic agent" denotes, in a manner known to those skilled in the art, any basic agent that fully dissociates in neutral aqueous solution or that has at least a high degree of dissociation in neutral aqueous solution. The expression "strong basic agent" in particular denotes sodium hydroxide, potassium hydroxide, lithium hydroxide and ammonium hydroxide.

The term "room temperature" means a temperature ranging from 20 to 25° C.

DETAILED DESCRIPTION OF THE INVENTION

Compound of formula (I)

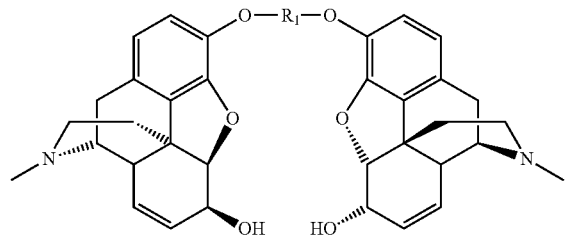

in which:

$R_1$ represents a carbonyl group, $COR_5CO$ in which $R_5$ represents a group ($C_1$-$C_4$)alkane-diyl, ($C_2$-$C_4$)alkene-diyl, ($C_2$-$C_4$)alkyne-diyl, hetero($C_{x1}$-$C_{y1}$)alkane-diyl, heterocyclo($C_3$-$C_6$)alkane-diyl, ($C_5$-$C_{14}$)arene-diyl, hetero($C_4$-$C_{10}$)arene-diyl bi($C_{10}$-$C_{16}$)arene-oxide-diyl or bi($C_{10}$-$C_{16}$)arene-diyl, $SO_2R_6SO_2$ in which $R_6$ represents a group ($C_1$-$C_4$)alkane-diyl, ($C_2$-$C_4$)alkene-diyl, ($C_2$-$C_4$)alkyne-diyl, hetero($C_1$-$C_4$)alkane-diyl, heterocyclo($C_3$-$C_6$)alkane-diyl, ($C_5$-$C_{14}$)arene-diyl, hetero($C_4$-$C_{10}$)arene-diyl, bi($C_{10}$-$C_{16}$)arene-oxide-diyl or bi($C_{10}$-$C_{16}$)arene-diyl.

Among the compounds of formula (I), mention may be made in particular of:
dimorphin-3-yl terephthalate,
dimorphin-3-yl isophthalate,
dimorphin-3-yl phthalate,
dimorphin-3-yl fumarate,
dimorphin-3-yl benzene-1,2-disulfonate,
dimorphin-3-yl benzene-1,3-disulfonate,
dimorphin-3-yl thiophene-2,5-dicarboxylate,
dimorphin-3-yl naphthalene-2,7-dicarboxylate,
dimorphin-3-yl 4,4'-oxybenzoate,
dimorphin-3-yl biphenyl-4,4'-dicarboxylate, and
dimorphin-3-yl carbonate.

The compound of formula (I) as defined previously may be prepared according to various processes, especially by esterification of the phenol group of morphine with a dicarboxylic acid and removal of the water by azeotropic distillation.

It may also be prepared according to the process described below.

According to one particular embodiment of the process of the present invention, it comprises, prior to step (i), the steps consisting in reacting a compound of formula $R_1Cl_2$ in which $R_1$ is as defined previously, with morphine in a two-phase medium comprising at least water, a strong basic agent and an aromatic solvent that is unsubstituted or substituted with one or more substituents chosen from the group formed by a halogen atom, a group ($C_1$-$C_4$)alkyl and a group ($C_1$-$C_4$)alkyloxy, said solvent having a melting point of less than or equal to −20° C.

In this procedure for preparing a compound of formula (I), the morphine is preferably introduced in excess relative to the compound of formula $R_1Cl_2$, for example in a mole ratio of 2.2 mol of morphine per 1 mol of compound $R_1Cl_2$.

The strong basic agent used may be sodium hydroxide.

Among the solvents that may be used in the process as defined above mention may be made in particular of chlorobenzene, toluene, 1,2-dichlorobenzene, 1,3,5-trifluorobenzene and mesitylene. Chlorobenzene is advantageously used, as it offers the best solubilization of the reagents.

Advantageously, the mixture of morphine and water is first prepared, and the strong basic agent is added thereto in an amount making it possible to obtain a pH greater than or equal to 10. The mixture is stirred until a homogeneous solution is obtained. The solvent and the compound of formula $R_1Cl_2$ are added to this uniform solution, preferably slowly and with vigorous stirring so as to enable the phase transfer.

A subject of the present invention is also the compounds corresponding to formula (I).

These compounds are useful as intermediates for synthesizing M6G or derivatives thereof.

Compound of Formula (II)

Glucuronic acid derivative corresponding to formula (II) below:

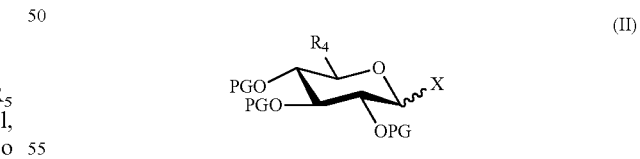

in which:

PG represents an acetyl, isobutyryl, benzoyl or pivaloyl group,

X represents a trihaloacetimidate group, and $R_4$ represents a group ($C_{x1}$-$C_{y1}$)alkylcarboxylate.

Among the glucuronic acid derivatives of formula (II), mention may be made in particular of those having one or more of the following characteristics:

PG represents an acetyl group,

X represents a group —OCNHCl$_3$ or a group —OCNPhCF$_3$, and $R_4$ represents a methylcarboxylate group.

According to one particular embodiment of the process according to the invention, the glucuronic acid derivative of formula (II) is methyl 2,3,4-tri-O-acetyl-α-D-glucopyranosyluronate trichloroacetimidate.

The compound of formula (II) may be prepared according to various processes that are well known to those skilled in the art.

For example, methyl 2,3,4-tri-O-acetyl-α-D-glucopyranosyluronate trichloroacetimidate may be synthesized according to the process described in Scheme 1 below:

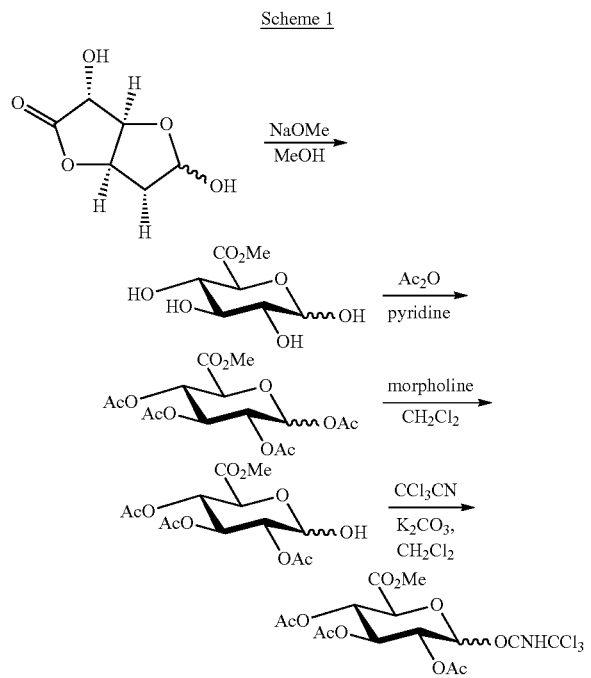

Such synthetic processes are described especially in Chem. Pharm. Bull. 53 (6) 684-687 (2005) for 2,3,4-tri-O-acetyl-α-D-glucopyranosyluronate trichloroacetimidate, in J. Chem. Soc. Perkin Trans. 1 1995 for the tri-O pivaloyl derivative, and in Liebigs Ann. Chem. 1983, 570-574 for the tri-O-benzoate derivative.

Parameters of Step (i)

As indicated previously, in the process of the invention, in step (i), a compound of formula (I) is reacted with a glucuronic acid derivative of formula (II) in the presence of an aromatic solvent and trimethylsilyl trifluoromethanesulfonate.

Among the aromatic solvents as defined previously that may be used, mention may be made in particular of chlorobenzene, toluene, 1,2-dichlorobenzene, 1,3,5-trifluorobenzene and mesitylene. Chlorobenzene is in particular advantageously used during step (i) and during the preparation of the compound of formula (I) as indicated previously.

According to one particular embodiment, the mole ratio of said derivative of formula (II) to said compound of formula (I) is between 2 and 5 and is in particular 4.

The reaction is performed in the presence of a weak Lewis acid, trimethylsilyl trifluoromethanesulfonate (TMSOTf).

The mole ratio of the TMSOTf to the compound of formula (I) is between 2.2 and 20 and is in particular 3.1.

According to one particular embodiment, the TMSOTf is introduced in two stages: a first portion is introduced into the solution of the product of formula (I) in the aromatic solvent prior to the addition of the glucuronic acid derivative, in order to salify the two nitrogens of the compound of formula (I), and the remaining portion is then introduced after the addition of the glucuronic acid derivative in order to perform the O-glycosylation.

Performing step (i) leads to the formation of the compound corresponding to formula (III) below:

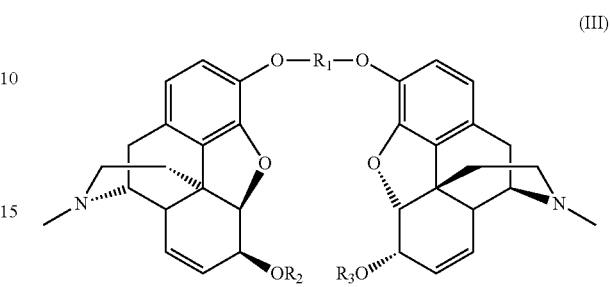

in which:
$R_1$ is as defined previously,
$R_2$ and $R_3$ independently represent a group PG as defined previously or a group corresponding to formula (IV) below:

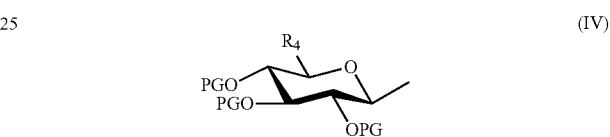

in which:
$R_4$ and PG are as defined previously,
with the proviso that at least one from among $R_2$ and $R_3$ represents a group of formula (IV).

A subject of the present invention is also the compounds corresponding to formula (III). These compounds are useful as intermediates for the synthesis of M6G or derivatives thereof.

Preferably, $R_2$ and $R_3$ both represent a group of formula (IV).

Among the compounds of formula (III) that are subjects of the invention, a first group of compounds has one or more of the following characteristics:
$R_1$ represents a terephthaloyl group,
at least one from among $R_2$ and $R_3$ represents a group of formula (IV) in which $R_4$ is a methyl 2,3,4-tri-O-acetyl-β-D-glucuropryranosyluronate group and PG is an acetyl group.

Among these compounds, mention may be made in particular of:
6-O-acetylmorphin-3-yl 6-O-(methyl 2,3,4-tri-O-acetyl-β-D-gluco-pyranosyluronate)morphin-3-yl terephthalate, and
bis[6-O-(methyl 2,3,4-tri-O-acetyl-β-D-glucopyranosyluronate)morphin-3-yl]terephthalate.

Parameters of Step (ii)

As indicated previously, the product obtained in step (i), i.e. the compound of formula (III), is reacted with a strong basic agent.

According to one particular embodiment, prior to the addition of the strong basic agent, the aromatic solvent is removed, according to methods known to those skilled in the art, for example by extracting the organic phase, optionally ending with evaporation under reduced pressure.

Generally, the compound of formula (III) is then dissolved in an aqueous-alcoholic mixture, for example in a methanol/water mixture, in a ratio ranging from 20/80 to 80/20, with stirring, until a uniform mixture is obtained.

This mixture is generally cooled to a temperature of less than or equal to 5° C.

The strong basic agent is then introduced into the mixture generally in an amount allowing a pH of greater than or equal to 10 and in particular greater than or equal to 12.5 to be obtained, preferably while maintaining the temperature at not more than 5° C.

According to one particular embodiment, the strong basic agent is sodium hydroxide.

The mixture obtained may then be heated, for example to 20° C., for a time that is sufficient to complete the reaction, for example for one hour.

When it is desired to obtain M6G or a derivative thereof in base form, the mixture, cooled beforehand, for example to a temperature of less than or equal to 5° C., is acidified so that it has a pH less than the $pK_a$ of the product to be synthesized, for example to pH 5.6. This acidification may be performed in particular by adding hydrochloric acid.

The mixture obtained may then be heated, for example to 20° C., for a time that is sufficient to complete the reaction, for example for 30 minutes.

Parameters of Step (iii)

The product obtained after step (ii) may be recovered in the form as obtained, i.e. in crude form, for example by filtration and then concentration of the filtrate under vacuum.

Advantageously, it may be recovered in purified form, which may be performed according to any purification method known to those skilled in the art, in particular by desalting, where appropriate followed by one or more steps of adsorption and desorption on ion-exchange resins and then optionally one or more dissolution/evaporation/crystallization cycles.

In order to reduce the salt content for the purpose especially of removing the residual sodium acetate and sodium terephthalate, the filtrate may, for example, be resuspended in alcohol, in particular in methanol, under conditions allowing the dissolution of the M6G or derivatives thereof, for example at 50° C. for 3 hours, and the mixture obtained may then be filtered to remove the solid particles and the residue obtained may be dried, for example by evaporation under reduced pressure.

The purification may be continued using ion-exchange resins. According to one particular embodiment, the residue obtained previously is resuspended in demineralized water, and the suspension is then acidified to a pH of between 2 and 4 and in particular greater than or equal to 3, for example by adding sulfuric acid, and is filtered, and the filtrate is placed in contact with a cationic resin under conditions allowing the adsorption of the M6G or derivative thereof, for example with stirring at 20° C. for 30 minutes, and is then filtered. These operations are repeated until the filtrate is depleted of M6G or the derivative thereof. The resins are then desorbed with a basic solution, for example with aqueous ammonia. The basic solution obtained is acidified to a pH of between 5 and 7 and in particular 6, and is then dried, for example by evaporation under reduced pressure.

Finally, this residue is resuspended in an aqueous-alcoholic mixture, for example in a methanol/water mixture, in a ratio ranging from 20/80 to 80/20, heated under conditions allowing its total dissolution, for example at reflux for 30 minutes, and the homogeneous mixture is then cooled slowly, for example to 0° C. over 2 hours, the first crystals appearing at 35° C.

The crystals are isolated, for example on a sinter funnel, washed, for example with methanol, and finally dried, for example by heating and evaporating under vacuum.

The invention is illustrated in a nonlimiting manner by the examples below.

EXAMPLES

Synthesis

Scheme 2 describes the synthesis of the intermediate compounds of formulae (I) and (III) and also of M6G and derivatives thereof.

In Scheme 2, the starting compounds and the reagents, when their mode of preparation is not described, are commercially available or described in the literature, or else may be prepared according to methods that are described therein or that are known to those skilled in the art.

Scheme 2

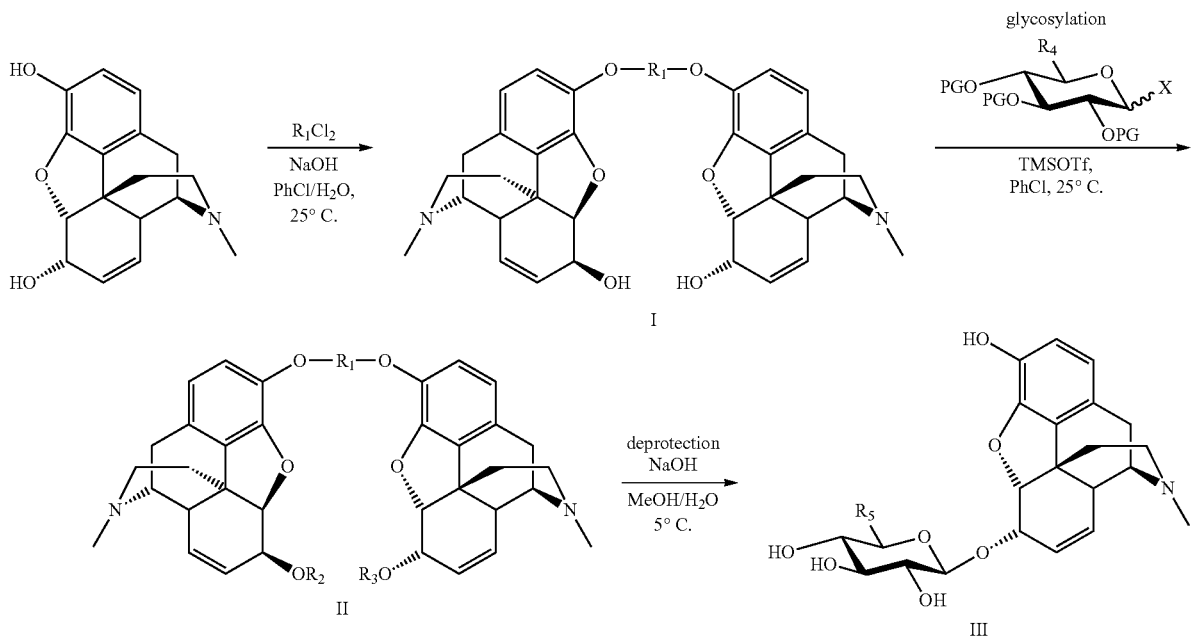

The examples that follow describe the preparation of certain compounds in accordance with the invention. These examples are not limiting, and serve merely to illustrate the present invention.

Preparation of Compounds of Formula (I)

Example 1

Dimorphin-3-yl terephthalate

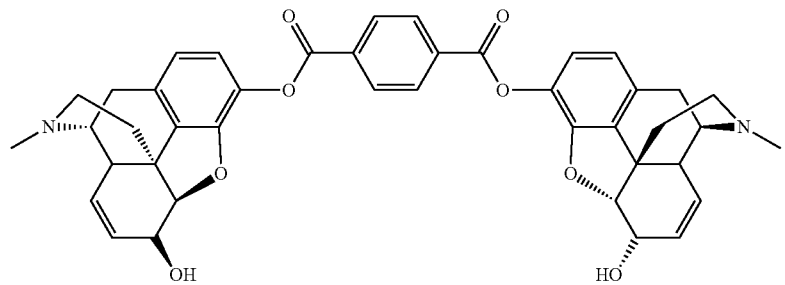

Terephthaloyl chloride (12.0 g, 0.0594 mol) is added portionwise over 2.5 hours to a solution of morphine monohydrate (40.0 g, 0.132 mol) in 0.66N sodium hydroxide (300 mL, 0.198 mol) and chlorobenzene (300 mL), at room temperature. The reaction medium is stirred for 15 minutes after the end of the addition.

The precipitate formed is filtered off and reslurried in a chlorobenzene/0.66 N sodium hydroxide mixture (300 mL/300 mL) and then washed with water (3×250 mL) to obtain the dimorphin-3-yl terephthalate in the form of white crystals (38.2 g, 92%).

$^1$H NMR (300 MHz, CDCl$_3$) δ 8.30 (s, 4H, CH-terephtalate), 6.87 (d, 2H, J 8.0 Hz, H-1), 6.67 (d, 2H, J 8.0 Hz, H-2), 5.83 (m, 2H, H-8), 5.32 (m, 2H, H-7), 4.95 (d, 2H, J 6.0 Hz, H-5), 4.20 (m, 2H, H-6), 3.40 (m, 2H, H-9), 3.10 (m, 2H, H-10a), 2.74 (m, 2H, H-14), 2.67-2.61 (m, 2H, H-16a), 2.47 (s, 6H, NCH$_3$), 2.42-2.31 (m, 4H, H-10b, H-16b), 2.13-2.05 (m, 2H, H-15a), 1.96-1.92 (m, 2H, H-15b).

$^{13}$C NMR (75 MHz, CDCl$_3$) δ 163.3 (C=O), 148.8 (C-ipso), 134.3 (C-8), 130.5 (CH-terephtalate), 129.7, 128.6 (C-ipso), 127.8 (C-7), 126.4 (C-ipso), 121.1 (C-1), 120.0 (C-2), 92.5 (C-5), 65.9 (C-6), 58.9 (C-9), 46.4 (C-16), 43.1 (NCH$_3$), 42.7 (C-13), 40.5 (C-14) 35.3 (C-15), 20.9 (C-10).

High Resolution Mass (ES)

Calculated for C$_{42}$H$_{42}$N$_2$O$_8$ [M+H$_2$]$^{2+}$: m/z=351.1471

Found: m/z=351.1467

The compounds of Examples 2 to 11 below were prepared in the same manner.

Example 2

Dimorphin-3-yl isophthalate

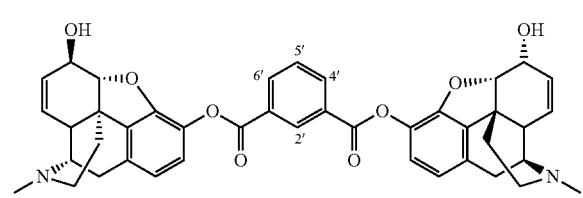

$^1$H NMR (300 MHz, CDCl$_3$) δ 9.00 (t, 1H, J 1.5 Hz, H-2'), 8.44 (dd, J 1.5 Hz, J 8.0 Hz, H-4', H-6'), 7.66 (t, 1H, J 8.0 Hz, H-5'), 6.87 (d, 2H, J 8.0 Hz, H-1), 6.67 (d, 2H, J 8.0 Hz, H-2), 5.83 (m, 2H, H-8), 5.32 (m, 2H, H-7), 4.95 (d, 2H, J 6.0 Hz, H-5), 4.20 (m, 2H, H-6), 3.40 (m, 2H, H-9), 3.09 (m, 2H, H-10a), 2.72 (m, 2H, H-14), 2.66-2.60 (m, 2H, H-16a), 2.47 (s, 6H, NCH$_3$), 2.43-2.30 (m, 4H, H-10b, H-16b), 2.15-2.04 (m, 2H, H-15a), 1.95-1.91 (m, 2H, H-15b).

Mass (chemical ionization): [M+H]$^+$=701.6

Example 3

Dimorphin-3-yl phthalate

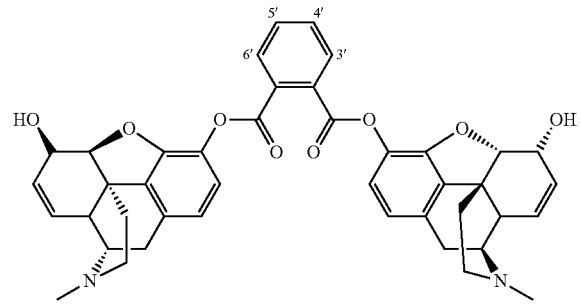

$^1$H NMR (300 MHz, CDCl$_3$) δ 7.97 (dd, 2H, J 3.5 Hz, J 6.0 Hz, H-3', H-6'), 7.67 (dd, J 3.5 Hz, J 6.0 Hz, H-4', H-5'), 6.87 (d, 2H, J 8.0 Hz, H-1), 6.59 (d, 2H, J 8.0 Hz, H-2), 5.74 (m, 2H, H-8), 5.29 (m, 2H, H-7), 4.81 (d, 2H, J 6.5 Hz, H-5), 4.15 (m, 2H, H-6), 3.37 (m, 2H, H-9), 3.06 (m, 2H, H-10a), 2.70 (m, 2H, H-14), 2.61-2.56 (m, 2H, H-16a), 2.44 (s, 6H, NCH$_3$), 2.42-2.27 (m, 4H, H-10b, H-16b), 2.08-2.05 (m, 2H, H-15a), 1.80 (m, 2H, H-15b).

Mass (chemical ionization): [M+H]$^+$=701.6

Example 4

Dimorphin-3-yl fumarate

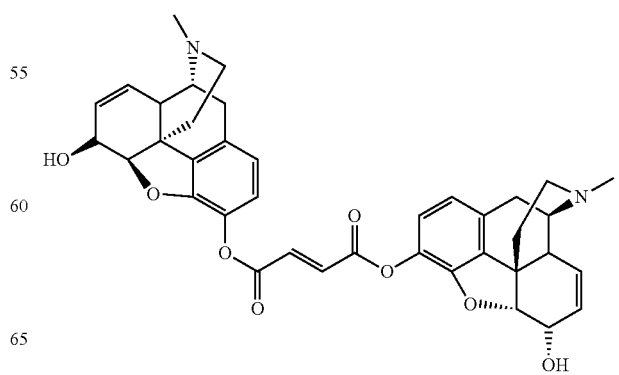

¹H NMR (300 MHz, CDCl₃) δ 7.23 (s, 2H, CHCOO), 6.81 (d, 2H, J 8.0 Hz, H-1), 6.64 (d, 2H, J 8.0 Hz, H-2), 5.78 (m, 2H, H-8), 5.30 (m, 2H, H-7), 4.95 (d, 2H, J 6.0 Hz, H-5), 4.19 (m, 2H, H-6), 3.42 (m, 2H, H-9), 3.08 (m, 2H, H-10a), 2.74 (m, 2H, H-14), 2.69-2.63 (m, 2H, H-16a), 2.47 (s, 6H, NCH₃), 2.42-2.30 (m, 4H, H-10b, H-16b), 2.16-2.06 (m, 2H, H-15a), 1.92 (m, 2H, H-15b).

Mass (chemical ionization): [M+H]⁺=651.6

Example 5

Dimorphin-3-yl benzene-1,2-disulfonate

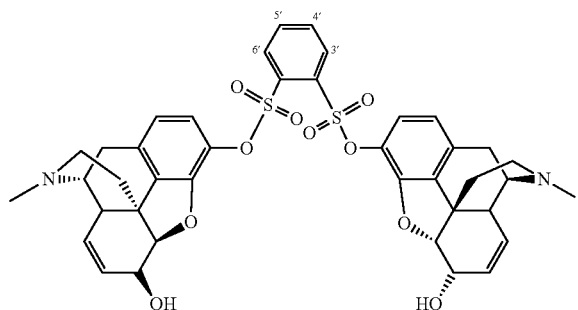

¹H NMR (300 MHz, CDCl₃) δ 8.24 (dd, 2H, J 3.5 Hz, J 6.0 Hz, H-3', H-6'), 7.77 (dd, J 3.5 Hz, J 6.0 Hz, H-4', H-5'), 6.79 (d, 2H, J 8.5 Hz, H-1), 6.51 (d, 2H, J 8.5 Hz, H-2), 5.69 (m, 2H, H-8), 5.22 (m, 2H, H-7), 4.81 (d, 2H, J 6.5 Hz, H-5), 4.15 (m, 2H, H-6), 3.35 (m, 2H, H-9), 3.02 (m, 2H, H-10a), 2.65 (m, 2H, H-14), 2.60-2.54 (m, 2H, H-16a), 2.41 (s, 6H, NCH₃), 2.40-2.22 (m, 4H, H-10b, H-16b), 2.05-2.00 (m, 2H, H-15a), 1.77-1.72 (m, 2H, H-15b).

Mass (chemical ionization): [M+H]⁺=773.6

Example 6

Dimorphin-3-yl benzene-1,3-disulfonate

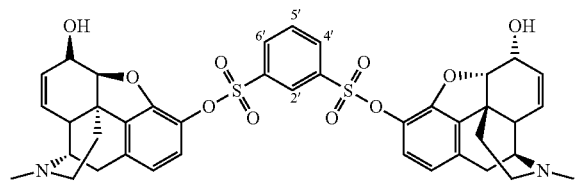

¹H NMR (300 MHz, CDCl₃) δ 8.24 (m, 3H, H-2', H-4', H-6'), 7.78 (t, 1H, J 8.5 Hz, H-5'), 6.51 (m, 4H, H-1, H-2), 5.66 (m, 2H, H-8), 5.27 (m, 2H, H-7), 4.85 (d, 2H, J 6.5 Hz, H-5), 4.15 (m, 2H, H-6), 3.34 (m, 2H, H-9), 3.03 (m, 2H, H-10a), 2.65 (m, 2H, H-14), 2.61-2.55 (m, 2H, H-16a), 2.42 (s, 6H, NCH₃), 2.35-2.24 (m, 4H, H-10b, H-16b), 2.09-1.99 (m, 2H, H-15a), 1.79-1.75 (m, 2H, H-15b).

Mass (chemical ionization): [M+H]⁺=773.6

Example 7

Dimorphin-3-yl thiophene-2,5-dicarboxylate

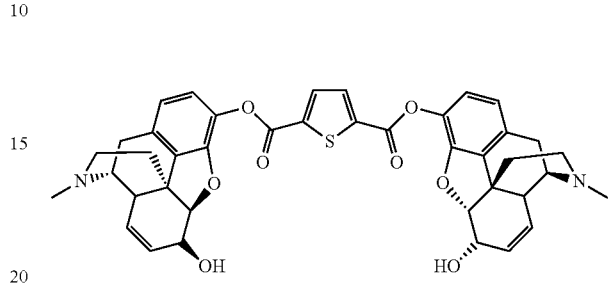

¹H NMR (300 MHz, CDCl₃) δ 7.95 (s, 2H, CH-thiophene), 6.86 (d, 1H, J 8.0 Hz, H-1), 6.66 (d, 2H, J 8.0 Hz, H-2), 5.79 (m, 2H, H-8), 5.30 (m, 2H, H-7), 4.95 (d, 2H, J 6.5 Hz, H-5), 4.18 (m, 2H, H-6), 3.40 (m, 2H, H-9), 3.09 (m, 2H, H-10a), 2.75 (m, 2H, H-14), 2.68-2.62 (m, 2H, H-16a), 2.41 (s, 6H, NCH₃), 2.40-2.30 (m, 4H, H-10b, H-16b), 2.14-2.05 (m, 2H, H-15a), 1.95-1.90 (m, 2H, H-15b).

Mass (chemical ionization): [M+H]⁺=708.6

Example 8

Dimorphin-3-yl naphthalene-2,7-dicarboxylate

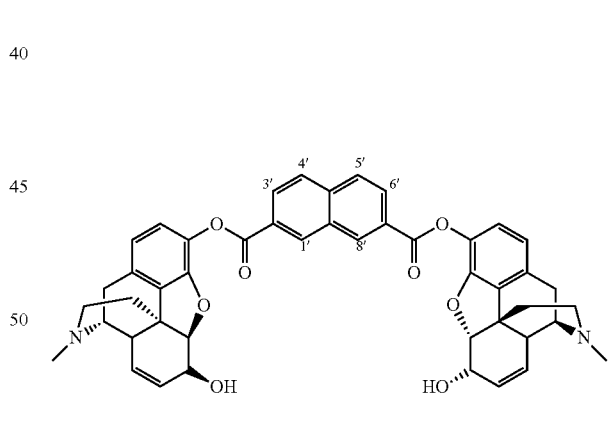

¹H NMR (300 MHz, CDCl₃) δ 8.83 (s, 2H, H-1', H-8'), 8.27 (dd, J 1.5 Hz, J 8.5 Hz, 2H, H-3', H-6'), 8.08 (d, 2H, J 8.5 Hz, H-4', H-5'), 6.92 (d, 1H, J 8.0 Hz, H-1), 6.69 (d, 2H, J 8.0 Hz, H-2), 5.84 (m, 2H, H-8), 5.34 (m, 2H, H-7), 4.95 (d, 2H, J 6.5 Hz, H-5), 4.20 (m, 2H, H-6), 3.40 (m, 2H, H-9), 3.11 (m, 2H, H-10a), 2.74 (m, 2H, H-14), 2.68-2.61 (m, 2H, H-16a), 2.47 (s, 6H, NCH₃), 2.44-2.32 (m, 4H, H-10b, H-16b), 2.14-2.05 (m, 2H, H-15a), 1.96-1.90 (m, 2H, H-15b).

Mass (chemical ionization): [M+H]⁺=751.6

Example 9

Dimorphin-3-yl 4,4'-oxybenzoate

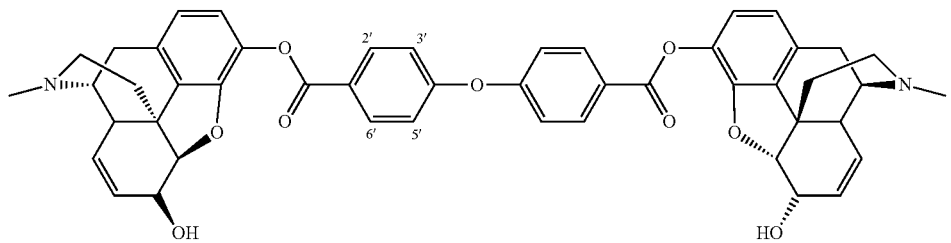

¹H NMR (300 MHz, CDCl₃) δ 8.16 (d, 4H, J 8.5 Hz, H-2', H-6'), 7.14 (d, 4H, J 8.5 Hz, H-3', H-5'), 6.87 (d, 2H, J 8.5 Hz, H-1), 6.67 (d, 2H, J 8.5 Hz, H-2), 5.82 (m, 2H, H-8), 5.31 (m, 2H, H-7), 4.95 (d, 2H, J 6.5 Hz, H-5), 4.20 (m, 2H, H-6), 3.40 (m, 2H, H-9), 3.10 (m, 2H, H-10a), 2.73 (m, 2H, H-14), 2.66-2.61 (m, 2H, H-16a), 2.42 (s, 6H, NCH₃), 2.40-2.30 (m, 4H, H-10b, H-16b), 2.18-2.10 (m, 2H, H-15a), 1.95-1.90 (m, 2H, H-15b).

Mass (chemical ionization): [M+H]⁺=793.5

Example 10

Dimorphin-3-yl biphenyl-4,4'-dicarboxylate

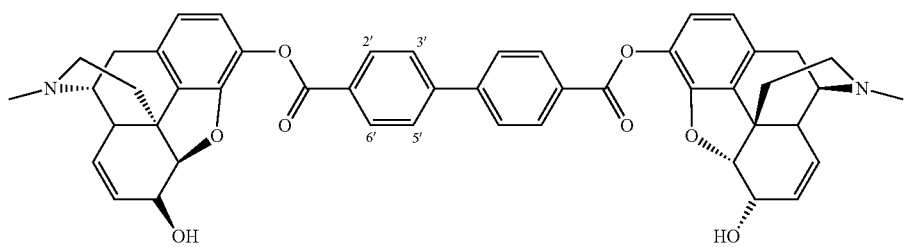

¹H NMR (300 MHz, CDCl₃) δ 8.25 (d, 4H, J 8.0 Hz, H-2', H-6'), 7.79 (d, 4H, J 8.0 Hz, H-3', H-5'), 6.90 (d, 2H, J 8.0 Hz, H-1), 6.68 (d, 2H, J 8.0 Hz, H-2), 5.84 (m, 2H, H-8), 5.32 (m, 2H, H-7), 4.95 (d, 2H, J 6.5 Hz, H-5), 4.22 (m, 2H, H-6), 3.41 (m, 2H, H-9), 3.11 (m, 2H, H-10a), 2.74 (m, 2H, H-14), 2.68-2.63 (m, 2H, H-16a), 2.43 (s, 6H, NCH₃), 2.42-2.32 (m, 4H, H-10b, H-16b), 2.17-2.11 (m, 2H, H-15a), 1.95-1.90 (m, 2H, H-15b).

Mass (chemical ionization): [M+H]⁺=777.5

Example 11

Dimorphin-3-yl carbonate

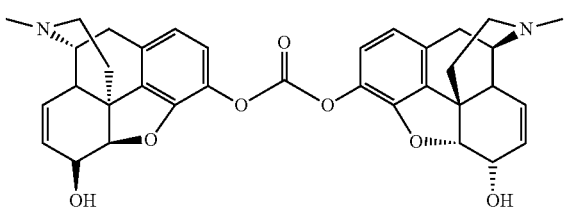

¹H NMR (300 MHz, CDCl₃) δ 6.88 (d, 2H, J 8.0 Hz, H-1), 6.59 (d, 2H, J 8.0 Hz, H-2), 5.70 (m, 2H, H-8), 5.23 (m, 2H, H-7), 4.97 (d, 2H, J 6.5 Hz, H-5), 4.15 (m, 2H, H-6), 3.36 (m, 2H, H-9), 3.11 (m, 2H, H-10a), 2.69 (m, 2H, H-14), 2.68-2.60 (m, 2H, H-16a), 2.43 (s, 6H, NCH₃), 2.40-2.27 (m, 4H, H-10b, H-16b), 2.10-2.04 (m, 2H, H-15a), 1.94-1.90 (m, 2H, H-15b).

Mass (chemical ionization): [M+H]⁺=597.5

Glycosylation

TMSOTf (27 μL, 0.15 mmol) is added to a solution of dimorphin-3-yl terephthalate (50 mg, 0.071 mmol) in chlorobenzene (4 mL) at room temperature. The reaction mixture is stirred for 3 minutes, followed by addition of methyl 2,3,4-tri-O-acetyl-α-D-glucopyranosyluronate trichloroacetimidate (171 mg, 0.36 mmol) and then TMSOTf (13 μL, 0.071 mmol).

The reaction medium is stirred for 30 minutes at room temperature.

NaHCO₃ (100 mg) is added, followed by CH₂Cl₂ (5 mL) and water (5 mL). The organic phase is separated out and dried over Na₂SO₄.

The solvent is removed under reduced pressure. A mixture of three products: bis[6-O-acetylmorphin-3-yl]terephthalate, 6-O-acetylmorphin-3-yl 6-O-(methyl 2,3,4-tri-O-acetyl-β-D-glucopyranosyluronate)morphin-3-yl terephthalate and bis[6-O-(methyl 2,3,4-tri-O-acetyl-β-D-glucopyranosyluronate)morphin-3-yl]terephthalate in Jul. 30, 1963 proportions is obtained.

Purification by reverse-phase preparative chromatography (95/5 to 20/80 (H₂O+0.1% TFA)/CH₃CN gradient) allows the three species to be isolated.

Example 12

Bis[6-O-acetylmorphin-3-yl]terephthalate

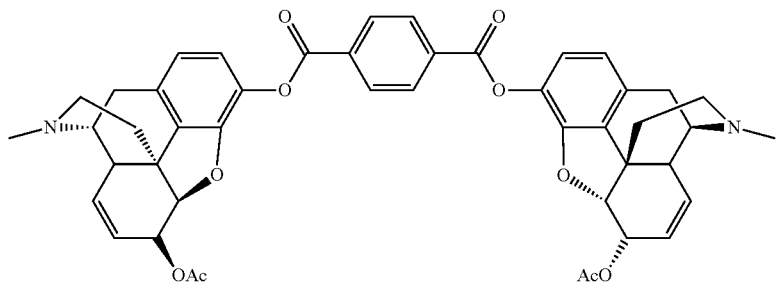

$^1$H NMR (300 MHz, CDCl$_3$) δ 8.30 (s, 4H, CH-terephtalate), 6.91 (d, 2H, J 8.0 Hz, H-1), 6.66 (d, 2H, J 8.0 Hz, H-2), 5.67 (m, 2H, H-8), 5.46 (m, 2H, H-7), 5.15 (m, 4H, H-5, H-6), 3.43 (m, 2H, H-9), 3.10 (m, 2H, H-10a), 2.81 (m, 2H, H-14), 2.67 (m, 2H, H-16a), 2.47 (s, 6H, NCH$_3$), 2.43-2.34 (m, 4H, H-10b, H-16b), 2.14-1.91 (m, 10H, CH$_3$CO, H-15).

$^{13}$C NMR (75 MHz, CDCl$_3$) δ 170.4, 163.2 (C=O), 149.5, 133.6, 132.5, 131.8, 131.6 (C-ipso), 130.3 (CH-terephtalate), 129.2 (C-7), 128.7 (C-8), 121.9 (C-1), 119.5 (C-2), 88.7 (C-5), 68.0 (C-6), 58.9 (C-9), 46.5 (C-16), 42.8 (NCH$_3$), 42.7 (C-13), 40.3 (C-14) 35.0 (C-15), 20.8 (C-10), 20.6 (CH$_3$CO).

High Resolution Mass (ES)
Calculated for C$_{46}$H$_{46}$N$_2$O$_{10}$ [M+H$_2$]$^{2+}$: m/z=393.1576
Found: m/z=393.1560

Example 13

6-O-Acetylmorphin-3-yl 6-O-(methyl 2,3,4-tri-O-acetyl-β-D-glucopyranosyluronate)morphin-3-yl terephthalate $^1$H NMR (300 MHz, CDCl$_3$) δ 8.31 (m, 4H, CH-terephtalate), 6.89 (m, 2H, H-1, H-1'), 6.65 (m, 2H, H-2, H-2'), 5.77 (m, 1H, H-8'), 5.68 (m, 1H, H-8), 5.46 (m, 1H, H-7), 5.33 (m, 1H, H-7'), 5.19 (m, 2H, H-3", H-4"), 5.15 (m, 1H, H-6), 4.96 (m, 3H, H-2", H-5, H-5'), 4.86 (d, 1H, J 7.5 Hz, H-1"), 4.31 (m, 1H, H-6'), 4.05 (m, 1H, H-5"), 3.72 (s, 3H, OCH$_3$), 3.48 (m, 2H, H-9, H-9'), 3.11 (m, 2H, H-10a, H-10a'), 2.85-2.65 (m, 4H, H-14, H-14', H-16a, H-16a'), 2.52-2.37 (m, 10H, NCH$_3$, H-10b, H-10b', H-16b, H-16b'), 2.15-1.85 (m, 13H, H-15, H-15', CH$_3$CO), 1.73 (s, 3H, CH$_3$CO).

$^{13}$C NMR (75 MHz, CDCl$_3$) δ 170.4, 170.1, 169.4, 169.0, 167.3, 163.6, 163.3 (C=O), 150.4, 149.5, 133.7, 133.6 (C-ipso), 132.0, 131.6, 130.8, 130.6, 130.3 129.0, 128.9 (CH-terephtalate, C-8, C-8', C-7, C-7', C-ipso), 122.2, 122.0 (C-1, C-1'), 119.6, 119.3 (C-2, C-2'), 99.3 (C-1"), 89.8, 88.7 (C-5, C-5'), 73.7 (C-6'), 72.7 (C-5"), 71.8 (C-3" or C-4"), 71.0 (C-2"), 69.4 (C-3" or C-4"), 67.9 (C-6), 59.0, 58.8 (C-9, C-9'), 46.6, 46.3 (C-16, C-16'), 42.8 (NCH$_3$), 40.6, 40.2 (C-14, C-14') 35.2, 34.9 (C-15, C-15'), 21.2, 21.0, 20.7, 20.6, 20.5, 20.4 (C-10, C-10' CH$_3$CO).

High Resolution Mass (ES)
Calculated for C$_{57}$H$_{60}$N$_2$O$_{18}$ [M+H$_2$]$^{2+}$: m/z=530.1921
Found: m/z=530.1918

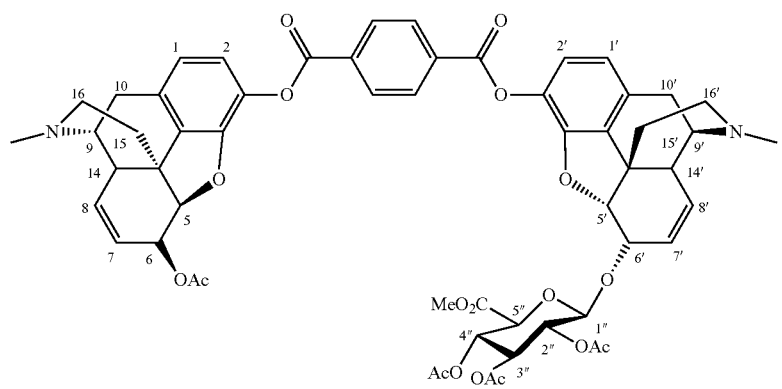

Example 14

Bis[6-O-(methyl 2,3,4-tri-O-acetyl-β-D-glucopyranosyl-uronate)morphin-3-yl]terephthalate

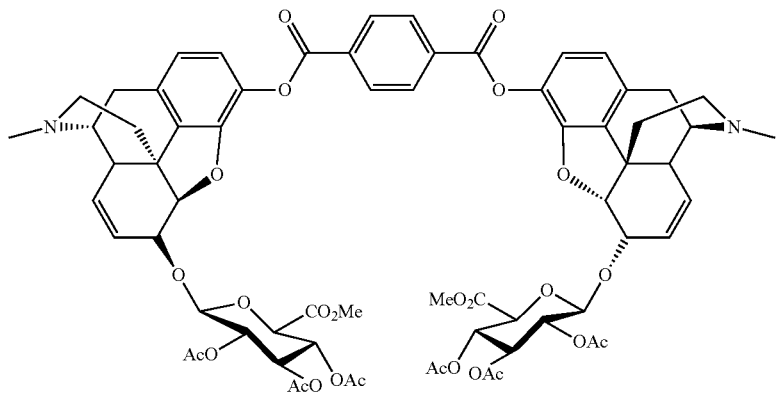

$^1$H NMR (300 MHz, CDCl$_3$) δ 8.34 (s, 4H, CH-terephtalate), 6.90 (d, 2H, J 8.0 Hz, H-1), 6.63 (d, 2H, J 8.0 Hz, H-2), 5.77 (m, 2H, H-8), 5.34 (m, 2H, H-7), 5.23 (m, 4H, H-3', H-4'), 5.02-4.94 (m, 4H, H-2', H-5), 4.86 (d, 2H, J 7.5 Hz, H-1'), 4.32 (m, 2H, H-6), 4.06 (d, 2H, J 9.5 Hz, H-5'), 3.72 (s, 6H, OCH$_3$), 3.48 (m, 2H, H-9), 3.11 (m, 2H, H-10a), 2.75-2.60 (m, 4H, H-14, H-16a), 2.51-2.25 (m, 10H, NCH$_3$, H-10b, H-16b), 2.16-1.90 (m, 16H, H-15, CH$_3$CO), 1.75 (s, 6H, CH$_3$CO).

$^{13}$C NMR (75 MHz, CDCl$_3$) δ 170.0, 169.4, 169.3, 167.4, 163.9 (C=O), 150.4, 133.7, 132.5, 131.7, 131.4 (C-ipso), 130.6 (CH-terephtalate, C-8), 128.9 (C-7), 122.0 (C-1), 119.3 (C-2), 99.2 (C-1'), 88.7 (C-5), 73.6 (C-6), 72.9 (C-5'), 71.7 (C-3' or C-4'), 70.9 (C-2'), 69.4 (C-3' or C-4'), 58.8 (C-9), 52.9 (OCH$_3$), 46.2 (C-16), 43.1 (NCH$_3$), 41.1 (C-14), 35.7 (C-15), 21.0 (C-10), 20.6, 20.5, 20.4 (CH$_3$CO).

High Resolution Mass (ES)

Calculated for C$_{68}$H$_{74}$N$_2$O$_{26}$ [M+H$_2$]$^{2+}$: m/z=667.2265

Found: m/z=667.2253

Saponification of the Intermediates Obtained from the O-Glycoside Coupling

After treatment and extraction of the organic phase (chlorobenzene) obtained from the coupling, the chlorobenzene is evaporated off under reduced pressure (15 mbar) to obtain a brownish oil (m=47.4 g). To this oil is added a mixture of methanol (140 ml) and demineralized water (35 ml) at 30° C., with stirring, until a homogeneous mixture is obtained. The mixture is then cooled to −5° C.

62.5 ml of concentrated sodium hydroxide solution (30% m/m) are added to this mixture, taking care not to exceed a temperature of 5° C. in the reactor. This mixture (pH=12.72) is then heated at 20° C. for 1 hour under nitrogen, and then cooled to −3° C.

37 ml of hydrochloric acid solution (37% HCl) are added to the mixture thus obtained (pH=5.6). The mixture is heated at 20° C. and maintained at this temperature for 30 minutes (pH stable at 5.6). The mixture is then filtered and the filtrate obtained is concentrated under vacuum (15 mbar) to obtain 67.0 g of dry extract.

Purification of the Residue Obtained from the Saponification and Acidification This residue is suspended in 500 ml of methanol at 50° C. for 3 hours (desalting) to obtain, after filtration and evaporation under reduced pressure (15 mbar), a residue of 30.8 g comprising a mixture of morphine analyzed by HPLC (of about 30%) and of M6G (of about 70%).

The residue obtained previously is suspended in 100 ml of demineralized water and the suspension obtained is acidified to pH 3.58 with 98% H$_2$SO$_4$ (2 ml) and then filtered.

6 g of the resin sold under the name "IRP 69" by the company Rohm & Haas are added to the filtrate (in a weight ratio of 3 relative to the weight of M6G contained according to the estimation obtained by HPLC). The heterogeneous mixture thus obtained is stirred at 20° C. for 30 minutes and then filtered.

The operation is repeated until the M6G contained has been depleted.

The resins obtained are desorbed with dilute aqueous ammonia (3% NH$_4$OH) and the basic solution obtained (pH=10.9) is neutralized to a pH of about 5 to 6 with dilute HCl.

The acidic aqueous solution obtained is evaporated under reduced pressure (15 mbar) to obtain 5.6 g of dry residue.

It is identified by HPLC (M6G content of about 80%).

Recrystallization of the M6G

The preceding dry residue (5.55 g) is suspended in a mixture of water (166.5 ml) and methanol (277.5 ml). The mixture is refluxed (90° C.) for 30 minutes and then cooled to 0° C. over 2 hours. The first crystals form at 35° C.

The crystals are isolated on a sinter funnel and then washed with 5 ml of methanol. After drying at 80° C. under 15 mbar, 2.6 g of pure M6G (organic purity >99%) are isolated.

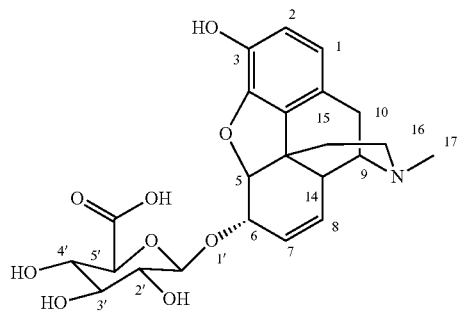

HPLC (M6G content)=98.6%

Mass (chemical ionization)=[M+H]+=462.2

$^{13}$C NMR (75 MHz, CDCl$_3$) (D$_2$O/exchange NaOD) δ (ppm±0.01 ppm): 129.71, 127.42 (C1, C2); 155, 73, 149.25

(C3, C4); 98.19 (C5); 111.12 (C1'); 85.82, 85.17, 82.94, 82.77, 81.40 (C6, C2', C3', C4', C5'); 68.66 (C9); 55.76 (C16); 52.07 (C13); 50.79 (C17); 48.34 (C14); 42.80 (C15); 30.70 (C10); 185.30 (CO$_2$H)

What is claimed is:

1. A process for preparing morphine-6-glucuronide or a derivative thereof, comprising:
   (i) reacting a compound of formula (I):

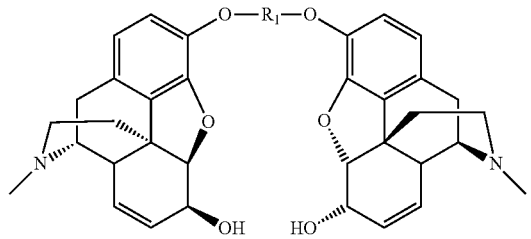

I wherein:
   $R_1$ represents a carbonyl group, COR$_5$CO in which $R_5$ represents a group (C$_1$-C$_4$)alkane-diyl, (C$_2$-C$_4$)alkene-diyl, (C$_2$-C$_4$)alkyne-diyl, hetero(C$_1$-C$_4$)alkane-diyl, heterocyclo(C$_3$-C$_6$)alkane-diyl, (C$_5$-C$_{14}$)arene-diyl, bi(C$_{10}$-C$_{16}$)arene-oxide-diyl, bi(C$_{10}$-C$_{16}$)arene-diyl, or hetero(C$_4$-C$_{10}$)arene-diyl, SO$_2$R$_6$SO$_2$ in which R$_6$ represents a group (C$_1$-C$_4$)alkane-diyl, (C$_2$-C$_4$)alkene-diyl, (C$_2$-C$_4$)alkyne-diyl, hetero(C$_1$-C$_4$)alkane-diyl, heterocyclo(C$_3$-C$_6$)alkane-diyl, (C$_5$-C$_{14}$)arene-diyl, hetero(C$_4$-C$_{10}$)arene-diyl, bi(C$_{10}$-C$_{16}$)arene-oxide-diyl or bi(C$_{10}$-C$_{16}$)arene-diyl;
   with a glucuronic acid derivative corresponding to formula (II):

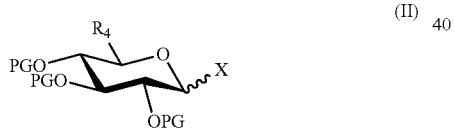

(II)

wherein:
PG represents an acetyl, isobutyryl, benzoyl or pivaloyl group,
X represents a trihaloacetimidate group, and
$R_4$ represents a group (C$_1$-C$_4$)alkylcarboxylate;
in the presence:
   of an aromatic solvent that is unsubstituted or substituted with one or more substituents chosen from the group formed by a halogen atom, a group (C$_1$-C$_4$) alkyl and a group (C$_1$-C$_4$)alkyloxy, said solvent having a melting point of less than or equal to −20° C., and
   of trimethylsilyl trifluoromethanesulfonate;
(ii) reacting the product obtained in step (i) with a strong basic agent; and then
(iii) recovering the product obtained in step (ii).

2. The preparation process according to claim 1, which comprises, prior to step (i), reacting a compound of formula R$_1$Cl$_2$ in which R$_1$ is as defined in claim 1 with morphine in a two-phase medium comprising at least water, a strong basic agent and an aromatic solvent that is unsubstituted or substituted with one or more solvents chosen from the group consisting of halogen atom, a group (C$_1$-C$_4$)alkyl and a group (C$_1$-C$_4$)alkyloxy, said solvent having a melting point of less than or equal to −20° C.

3. The process according to claim 1 wherein said compound of formula (I) is selected from the group consisting of:
   dimorphin-3-yl terephthalate,
   dimorphin-3-yl isophthalate,
   dimorphin-3-yl phthalate,
   dimorphin-3-yl fumarate,
   dimorphin-3-yl benzene-1,2-disulfonate,
   dimorphin-3-yl benzene-1,3-disulfonate,
   dimorphin-3-yl thiophene-2,5-dicarboxylate,
   dimorphin-3-yl naphthalene-2,7-dicarboxylate,
   dimorphin-3-yl 4,4'-oxybenzoate,
   dimorphin-3-yl biphenyl-4,4'-dicarboxylate, and
   dimorphin-3-yl carbonate.

4. The process according to claim 1, wherein said compound of formula (II) has one or more of the following characteristics:
   PG represents an acetyl group,
   X represents a group —OCNHCl$_3$ or a group —OCN-PhCF$_3$, and
   $R_4$ represents a methylcarboxylate group.

5. The process according to claim 1, wherein said compound of formula (II) is methyl 2,3,4-tri-O-acetyl-α-D-glucopyranosyluronate trichloroacetimidate.

6. The process according to claim 1 wherein said aromatic solvent is chosen from chlorobenzene, toluene, 1,2-dichlorobenzene, 1,3,5-trifluorobenzene and mesitylene.

7. The process according to claim 1 wherein said strong basic agent is sodium hydroxide.

8. The process according to claim 1 wherein the mole ratio of said glucuronic acid derivative of formula (II) to said compound of formula (I) is between 2 and 5.

9. The process according to claim 1 wherein the mole ratio of the trimethylsilyl trifluoromethanesulfonate to said compound of formula (I) is between 2.2 and 20.

10. A compound of formula

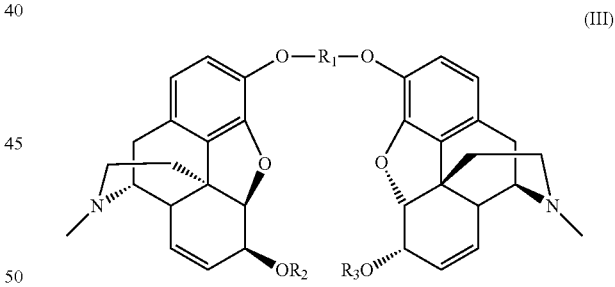

(III)

wherein:
$R_1$ is as defined in claim 1,
$R_2$ and $R_3$ independently represent a group PG as defined in claim 1 or a group of formula (IV) below:

(IV)

in which:
$R_4$ and PG are as defined in claim 1,
with the proviso that at least one from among $R_2$ and $R_3$ represents a group of formula (IV).

11. The compound according to claim 10, wherein said compound has one or more of the following characteristics:
$R_1$ represents a terephthaloyl group, and
at least one from among $R_2$ and $R_3$ represents a group of formula (IV) in which $R_4$ is a methyl 2,3,4-tri-O-acetyl-β-D-glucuropryranosyluronate group and PG is an acetyl group.

12. The compound according to claim 10, selected from the group consisting of:
6-O-acetylmorphin-3-yl 6-O-(methyl 2,3,4-tri-O-acetyl-β-D-glucopyranosyluronate)morphin-3-yl terephthalate, and
bis[6-O-(methyl 2,3,4-tri-O-acetyl-β-D-glucopyranosyluronate)morphin-3-yl]terephthalate.

13. A compound of formula

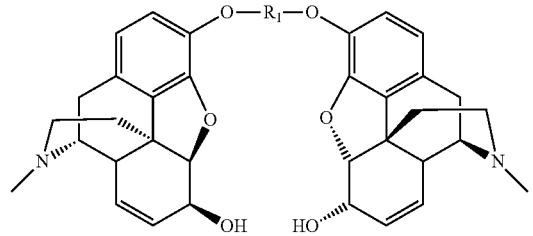

I wherein:
$R_1$ represents a carbonyl group, $COR_5CO$ in which $R_5$ represents a group $C_2$-$C_4$ alkene-diyl, ($C_2$-$C_4$)alkyne-diyl, hetero $C_1$-$C_4$ alkane-diyl, heterocyclo($C_3$-$C_6$)alkane-diyl, $C_5$-$C_{14}$ arene-diyl, bi($C_{10}$-$C_{16}$ arene-oxide-diyl, bi($C_{10}$-$C_{16}$ arene-diyl, or hetero($C_4$-$C_{10}$)arene-diyl, $SO_2R_6SO_2$ in which $R_6$ resents a group ($C_1$-$C_4$) alkane-diyl, ($C_2$-$C_4$)arene-diyl, ($C_2$-$C_4$)alkyne-diyl, hetero($C_1$-$C_4$ alkane-diyl, heterocyclo($C_3$-$C_6$)alkane-diyl, ($C_5$-$C_{14}$)arene-diyl, hetero($C_4$-$C_{10}$)arene-diyl, bi($C_{10}$-$C_{16}$)arene-oxide-diyl or bi($C_{10}$-$C_{16}$)arene-diyl.

14. The compound according to claim 13, selected from the group consisting of:
dimorphin-3-yl terephthalate,
dimorphin-3-yl isophthalate,
dimorphin-3-yl phthalate,
dimorphin-3-yl fumarate,
dimorphin-3-yl benzene-1,2-disulfonate,
dimorphin-3-yl benzene-1,3-disulfonate,
dimorphin-3-yl thiophene-2,5-dicarboxylate,
dimorphin-3-yl naphthalene-2,7-dicarboxylate,
dimorphin-3-yl 4,4'-oxybenzoate,
dimorphin-3-yl biphenyl-4,4'-dicarboxylate, and
dimorphin-3-yl carbonate.

\* \* \* \* \*